United States Patent [19]

Siegal

[11] Patent Number: 5,374,267
[45] Date of Patent: Dec. 20, 1994

[54] DEVICE FOR FIXING AT LEAST A PART OF THE HUMAN CERVICAL AND/OR THORACIC VERTEBRAL COLUMN

[75] Inventor: Tzony Siegal, Jeruzalem, Israel

[73] Assignee: Acromed B.V., Netherlands

[21] Appl. No.: 19,169

[22] Filed: Feb. 17, 1993

[30] Foreign Application Priority Data

Feb. 17, 1992 [NL] Netherlands ............... 9200288

[51] Int. Cl.$^5$ ............................................. A61B 17/58
[52] U.S. Cl. ....................................................... 606/61
[58] Field of Search ................. 606/61, 60, 72, 74, 606/75, 105, 53

[56] References Cited

U.S. PATENT DOCUMENTS

| | | | |
|---|---|---|---|
| 4,269,178 | 5/1981 | Keene | 606/61 |
| 4,361,141 | 11/1982 | Tanner . | |
| 4,422,451 | 12/1983 | Kalamchi | 606/61 |
| 4,567,884 | 2/1986 | Edwards | 606/61 |
| 5,005,562 | 4/1991 | Cotrel . | |
| 5,024,213 | 6/1991 | Asher et al. | 606/61 |
| 5,067,955 | 11/1991 | Cotrel . | |

FOREIGN PATENT DOCUMENTS

| | | |
|---|---|---|
| 0348272 | 12/1989 | European Pat. Off. . |
| 0384001 | 8/1990 | European Pat. Off. . |
| 0392927 | 10/1990 | European Pat. Off. . |
| 2642642 | 8/1990 | France ............ 606/61 |
| 1472097 | 4/1977 | United Kingdom . |
| 2131300 | 6/1984 | United Kingdom . |

OTHER PUBLICATIONS

Ghista, D. N., et al., "Biomechanical Analyses of Some Instrumentations for Stabilization of Dorso-Lumbar Spinal Injuries", 2200 Medical & Biological Engineering & Computing, vol. 21 (1983) Jul., No. 4, Stevenage, Herts, Great-Britain, pp. 494–502.

Primary Examiner—Tamara L. Graysay
Attorney, Agent, or Firm—Larson and Taylor

[57] ABSTRACT

A device for fixing at least a part of the human cervical and/or thoracic vertebral column comprises at least one assembly of a plurality of fixation elements (1, 1a and 1b, 1c, respectively) arranged above each other and at least one rod or wire (2, 2a) interconnecting these fixation elements. Each fixation element comprises a substantially block-shaped body (4) and a hook projecting from the lower edge area (5) of the block-shaped body (4). A first articular process contact surface (7) is constituted by an upright side of the block-shaped body (4) that faces the hook. A second articular process contact surface (8) is constituted by the substantially upwardly directed surface of the hook (6). The first (7) and the second articular process contact surfaces (8) include an acute angle ($\alpha$) and a securing means (9), in a securing position, extends into the space included by the first (7) and the second (8) vertebra contact surfaces.

9 Claims, 6 Drawing Sheets

FIG. 11

DEVICE FOR FIXING AT LEAST A PART OF THE HUMAN CERVICAL AND/OR THORACIC VERTEBRAL COLUMN

FIELD OF THE INVENTION

This invention relates to a device for fixing at least a part of the human vertebral column, comprising at least one assembly of a plurality of fixation elements arranged above each other and at least one rod or wire interconnecting these fixation elements, each fixation element comprising a substantially block-shaped body and a hook extending from the lower edge area of the block-shaped body, a first vertebra contact surface being constituted by an upright side of the block-shaped body that faces the hook and a second vertebra contact surface being constituted by a substantially upwardly directed surface of the hook, whilst a securing means, in a securing position, extends at least partly into the space between the first and the second vertebra contact surfaces.

BACKGROUND OF THE INVENTION

Such a device is already utilized in practice for fixing the lumbar and the lower thoracic vertebrae and is described, for instance, in French patent application 2,642,642. The hook of each fixation element, which is U-shaped for this application, extends between two vertebrae from a point between the spinous processes and the transverse processes of a vertebra in the direction of the spinal canal. When a fixation element is thus arranged, the substantially block-shaped body is disposed against the exterior of the vertebra located above the hook. Two fixation elements arranged above each other and thus attached to the vertebral column are connected together by means of a rod. The securing means is situated in cortical bone only at the first vertebra contact surface and for the rest the securing means extends into spongy bone, which is rather weak. The drawback of this is that the securing pin can only transmit a minor couple to the vertebra and will loosen in the course of time.

As regards the fixation of the cervical and upper thoracic vertebrae, however, the space between the spinous process and the transverse processes for accommodating the block-shaped body is lacking and further the bone mass of the vertebrae is too small for the hook to be arranged between the vertebrae in the manner described. The fact is that the diameter of the spinal canal relative to the outer diameter of the vertebrae is much greater in the cervical and upper thoracic vertebrae than in the lower thoracic and lumbar vertebrae.

For that reason, when fixing cervical and/or upper thoracic vertebrae, which is for instance necessary in the case of fracture or congenital disorders leading to deviation of the cervical and/or thoracic vertebral column, heretofore a makeshift fixation has been effected with plates, screws, wires and the like. A disadvantage of this makeshift fixation is that screws, for instance, weaken the cervical and thoracic vertebrae and that a positive result of a surgical treatment for realizing such makeshift fixation cannot be guaranteed for a prolonged time.

SUMMARY OF THE INVENTION

The object of the invention is to provide a durable fixation of at least a part of the cervical and/or thoracic vertebral column without the above-described disadvantages.

To that end, a device of the type described in the opening paragraph hereof is characterized in that the vertebra contact surfaces are substantially flat articular process contact surfaces including a V-shaped space, the first and the second articular process contact surfaces being interconnected through a small radius. The V-shaped space included by the fixation means substantially corresponds with the shape of an articular process of a thoracic or cervical vertebra to be received therein, and the fixation element is therefore particularly suitable for gripping the articular processes of the cervical and thoracic vertebrae. The articular processes are located at the back of the vertebral body at the junction of the vertebral body and the transverse processes. When the fixation elements of the device are fitted onto the articular processes, the articular process contact surfaces of the fixation elements are located substantially against the articular processes. The securing means referred to enables attachment of the fixation elements to the articular process.

A particularly good grip of the articular processes by the fixation elements can be obtained when the angle of the V-shaped space included by the articular process contact surfaces is in the range of 40°–50°.

To ensure that the fixation elements are optimally secured to the articular processes, the securing means may be constructed, in accordance with a further elaboration of the invention, as a securing pin, which is mounted in the block-shaped body so as to be movable in the direction of its longitudinal axis and extends substantially perpendicularly to the first vertebra contact surface, whilst, in the securing position, the end of the securing pin remote from the block-shaped body is located close to the free end of the hook.

When the above-described securing pin has been driven into the body of the articular process, both the part of the securing pin located proximal to the block-shaped body and the part of the securing pin located proximal to the free end of the hook are situated in the cortical bone of the articular process. The securing provision thus obtained is capable of taking up considerable couple.

The fixation elements may comprise means for detachably connecting the rod interconnecting the fixation elements, these means comprising at least a bore for receiving the rod or wire, extending throughout the height of the substantially block-shaped body. It is particularly advantageous when, in accordance with a further elaboration of the invention, the position of the bore with respect to the securing means extending into the space included between the first and second articular process contact surfaces is such that a rod or wire arranged in the bore fixes the securing means in its securing position. As a result, it is impossible for the securing means to loosen in the course of time and it is ensured that the fixation elements are stably secured to the articular processes.

Especially with a view to promoting ease of mounting the device on a vertebral element, it is particularly advantageous when, in accordance with a further elaboration of the invention, the bore forms part of a substantially L-shaped slot extending through the block-shaped body throughout the height of the fixation element, a first leg of this slot terminating in a side surface of the block-shaped body that bounds the first articular process contact surface, where it constitutes a receiving slot for the rod or wire, whilst a second leg thereof extends in the direction of the hook and terminates in the bore, the rod or wire being fixable in the bore with a retaining screw fitted in the rear wall in line with the second leg and extending into the L-shaped slot.

The receiving slot in the side surface of the block-shaped body enables lateral insertion of the wire or rod into the fixation element. As a consequence, the magnitude of the incision to be made to allow the device to be fitted is limited to a minimum.

In general, it will be necessary to fix the cervical or thoracic vertebral column on opposite sides, i.e., both on the left and on the right. This is already known with respect to fixing lower thoracic and lumbar vertebrae in that the assemblies of fixation elements, arranged above each other, and the rod or wire interconnecting these fixation elements are interconnected by means of at least one transverse rod or transverse wire mounted on the respective rods or wires. Since there is no space for fitting a transverse rod or wire to the respective rods or wires of the assemblies at the cervical vertebral column, on account of the spinous processes, it is particularly advantageous when, in accordance with a further elaboration of the invention, at least two fixation elements of the respective assemblies, which are located at the same level, are provided with transverse connector means interconnecting the two assemblies through cooperation with the transverse rod or transverse wire.

For the same reasons that apply in the case of fixation of the rod or wire that extends in longitudinal direction, the transverse rod connector means may be constructed as a substantially L-shaped slot extending through the block-shaped body throughout the width of the fixation element, a first leg of this slot terminating in the bottom surface of the block-shaped body, where it constitutes a receiving slot for the transverse rod or wire, whilst a second leg thereof extends in the direction of the hook, the transverse rod being fixable in the second leg of the L-shaped slot with a retaining screw fitted in the rear wall in line with the second leg and extending into the L-shaped slot.

The two L-shaped slots may be provided with a local recess provided opposite the retaining screw so as to guarantee good fixation of the rod or wire with respect to the fixation element in the manner disclosed in U.S. Pat. No. 5,024,213 to Asher et al., issued on Jun. 18, 1991.

BRIEF DESCRIPTION OF THE DRAWINGS

To clarify the invention, two exemplary embodiments of the device will now be described with reference to the accompanying drawings.

DESCRIPTION OF THE PREFERRED EMBODIMENTS

Figure 1:
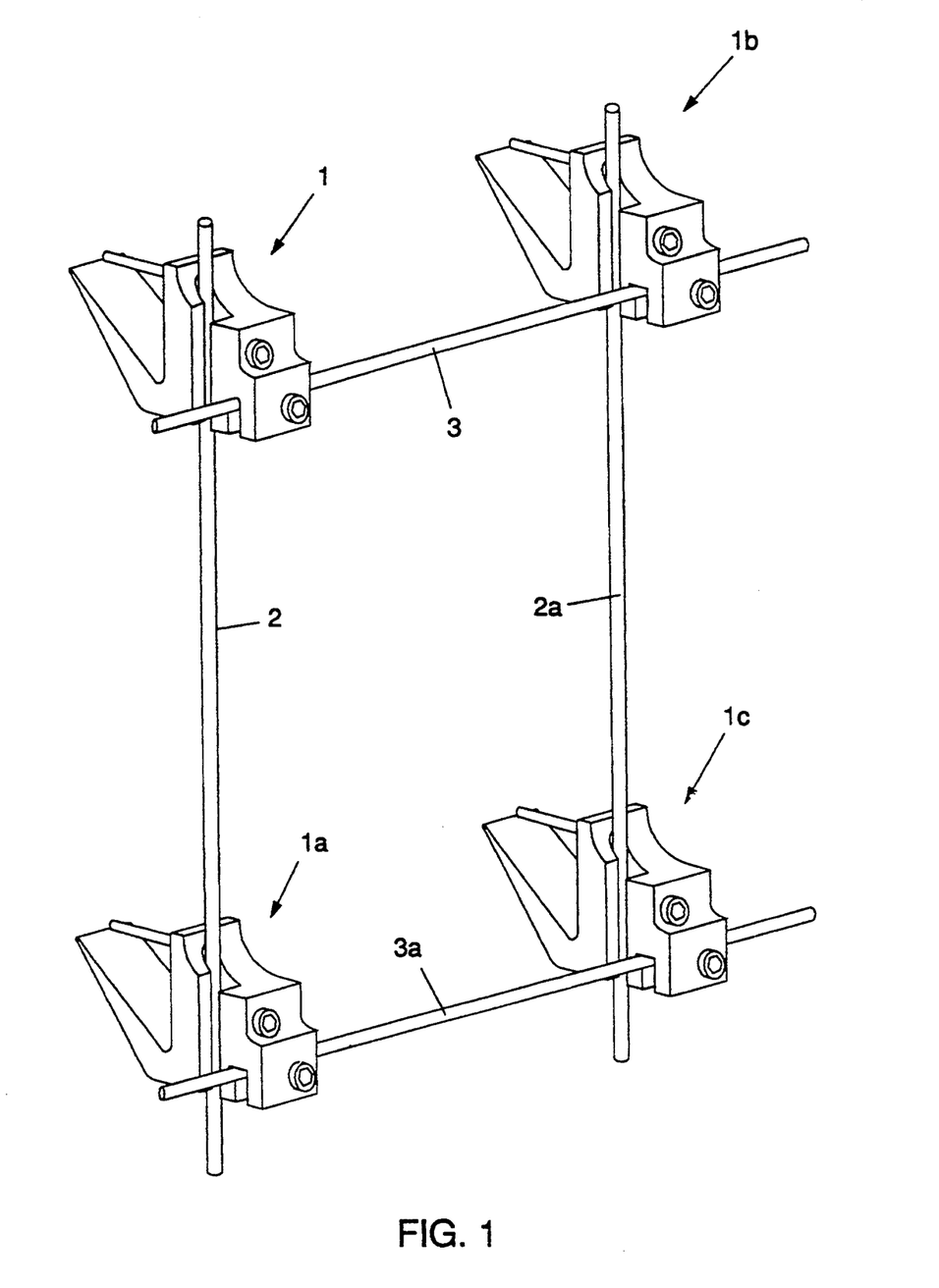
FIG. 1 is a perspective view of an exemplary embodiment of the device, particularly suitable for the fixation of the cervical vertebral column, the device comprising four fixation elements interconnected by means of longitudinal and transverse wires.
Figure 2:
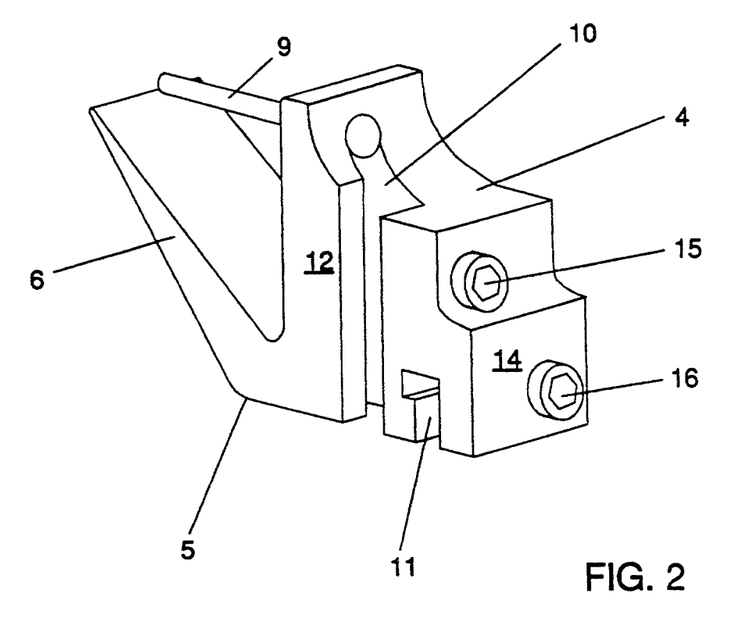
FIG. 2 is a perspective view of an exemplary embodiment of a fixation element as used in the device as shown in FIG. 1.
Figure 3:
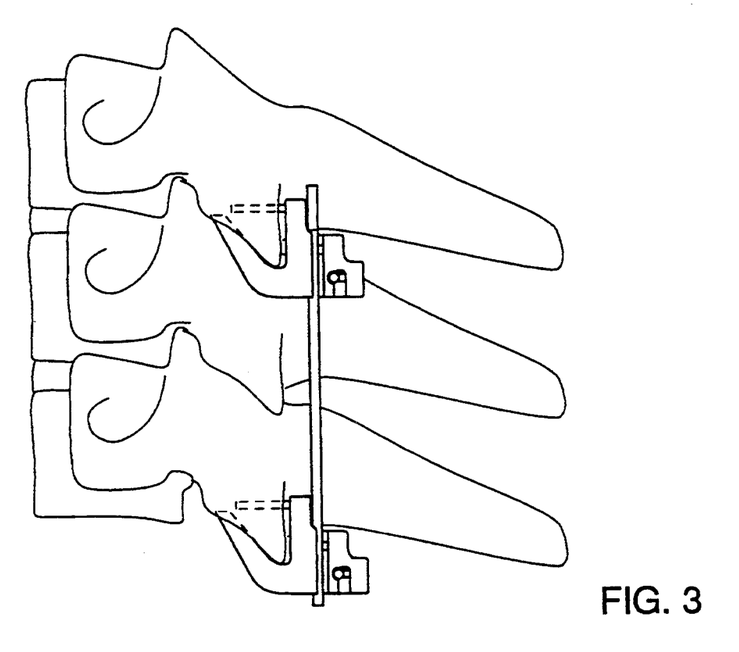
FIG. 3 is a side elevation of the device shown in FIG. 1, mounted on a cervical vertebral column.
Figure 4:
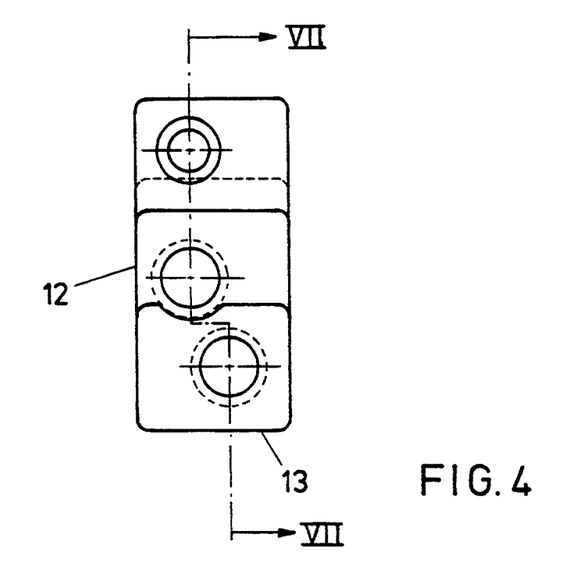
FIG. 4 is a rear view of an embodiment of a fixation element as shown in FIG. 2.
Figure 5:
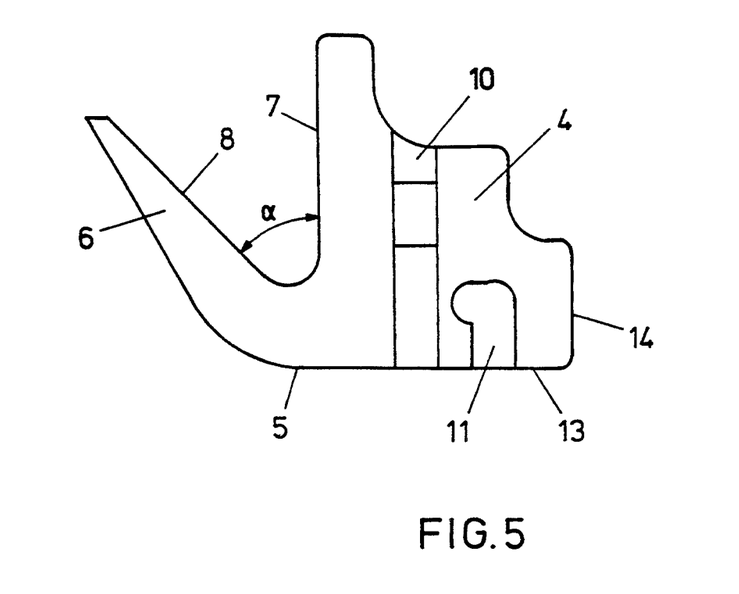
FIG. 5 is a side elevation of the fixation element shown in FIG. 4.
Figure 6:
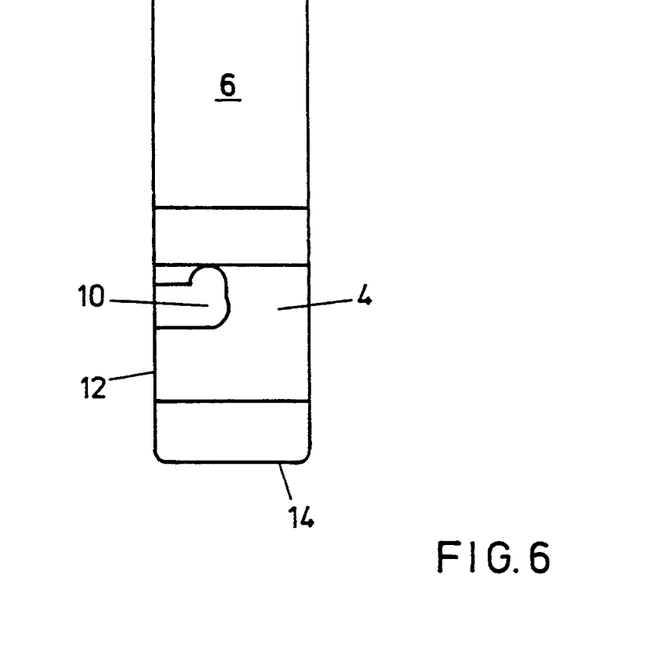
FIG. 6 is a top plan view of the fixation element shown in FIG. 4.
Figure 7:
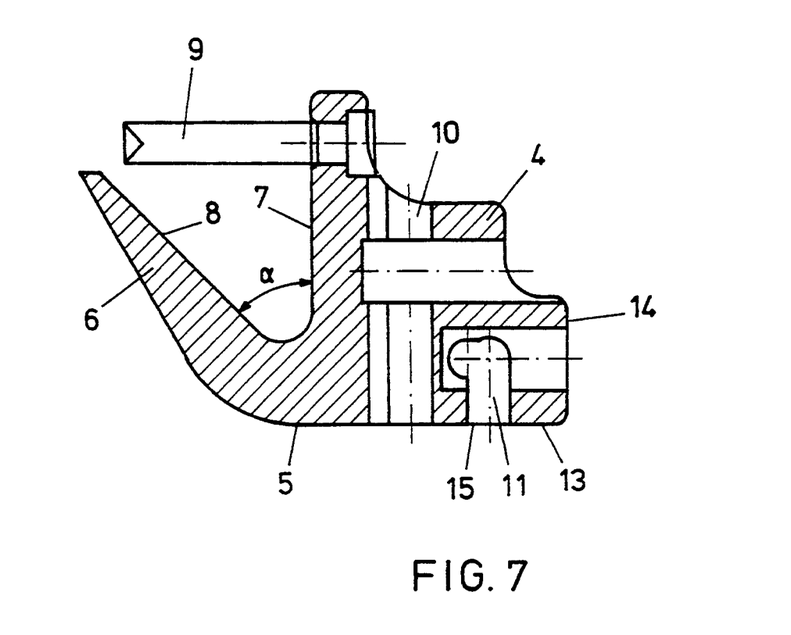
FIG. 7 is a sectional view taken along line VII—VII of FIG. 4.
Figure 8:
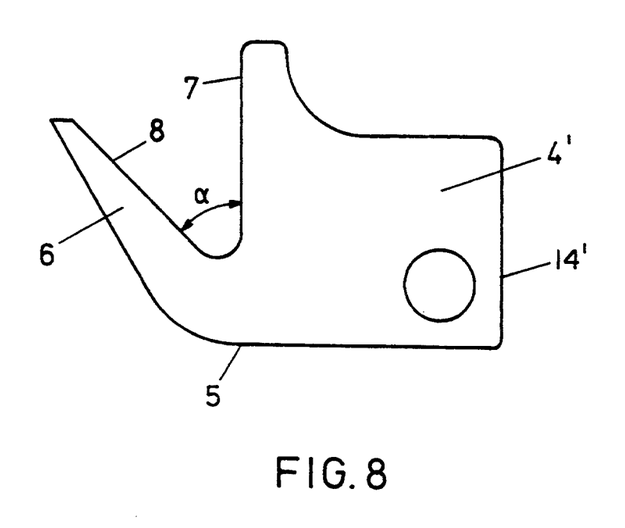
FIG. 8 is a side elevation of another exemplary embodiment of a fixation element, which is particularly suitable for fixing the thoracic vertebral column.
Figure 9:
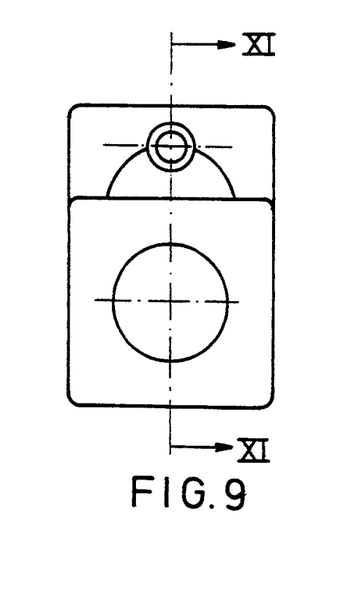
FIG. 9 is a rear view of the fixation element shown in FIG. 8.
Figure 10:
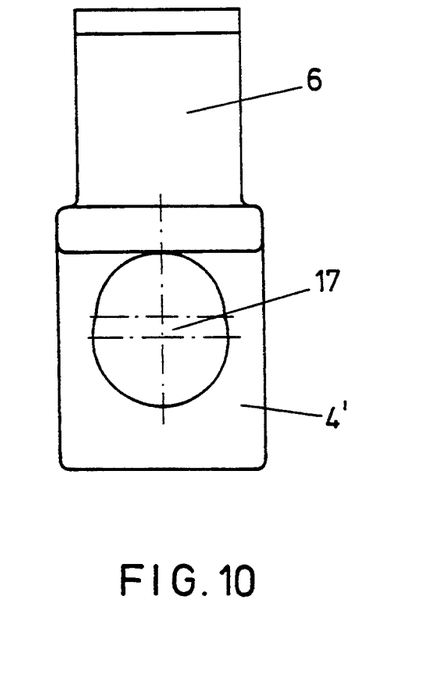
FIG. 10 is a top plan view of the fixation element shown in FIG. 8.
Figure 11:
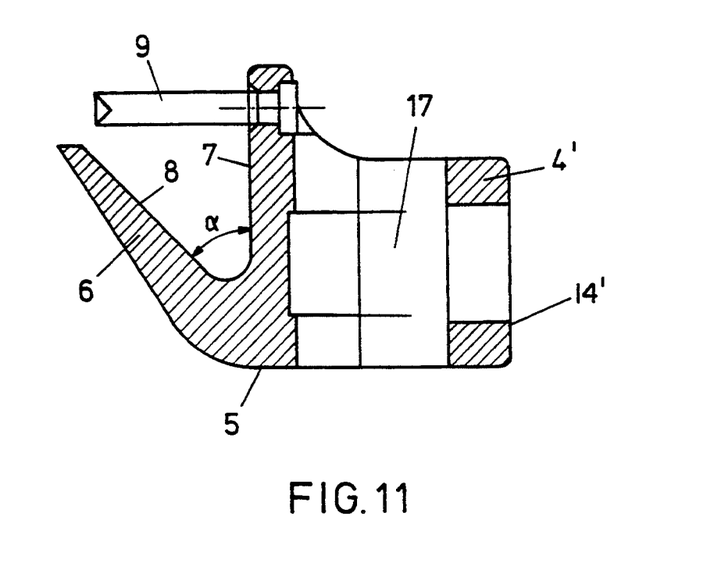
FIG. 11 is a sectional view taken along the line XI—XI of FIG. 9.

FIG. 1 is an overall view of an exemplary embodiment of the present device, showing four fixation elements 1, 1a, 1b, 1c connected together through longitudinal rods or wires 2, 2a and transverse rods or wires 3, 3a, thus forming a rigid frame, which, when fitted on the cervical and/or thoracic part of the vertebral column, is capable of fixing two or more vertebral elements with respect to each other. For the transverse and longitudinal rods or wires 2, 2a, 3, 3a, it is for instance possible to use wires sold under the trademark "KIRCHNER", which are known from practice. It will be clear that the device may comprise more than two fixation elements arranged above each other. Thus, the device may for instance comprise six or more fixation elements. With a device comprising six or more fixation elements, three or more vertebrae can be fixed. Also, the device may exclusively comprise the fixation elements 1, 1a, arranged above each other, and a rod or wire 2 connecting the fixation elements together. In that case, the device is arranged on only one side of the vertebral column, the rods or wires 2a, 3, 3a and the fixation elements 1b and 1c being absent.

A fixation element of the device as shown in FIG. 1 is shown separately in FIGS. 2 and 4-7. The fixation element comprises a substantially block-shaped body 4 and a hook 6 projecting from the lower edge 5 of the block-shaped body 4. This fixation element, which is particularly suitable for fixation of the thoracic and/or cervical vertebrae grips an articular process of these vertebrae. A first articular process contact surface 7 is constituted by the upright side of the block-shaped body 4 that faces the hook 6, and a second articular process contact surface 8 is constituted by the surface of the hook 6 that faces substantially upwards. In mounted position, contact surfaces 7 and 8 abut two surfaces of an articular process of a cervical or thoracic vertebra. According to the invention, the articular process contact surfaces include a V-shaped space of an angle $\alpha$, which is 45° in the exemplary embodiments, and a securing means 9 extends into the space included by the first and second articular process contact surfaces 7, 8, respectively. The securing means is constructed as a securing pin 9, which is mounted in the block-shaped body 4 so as to be movable in the direction of its longitudinal axis, this securing member 9 extending substantially perpendicularly to the first articular process contact surface 7. In the securing position, the end of the securing pin 9 remote from the block-shaped body 4 is located close to the free end of the hook 6. Before the fixation elements are fitted onto the articular processes, the securing pin 9 is in a rearmost position where the space enclosed by the articular process contact surfaces 7, 8 is left clear. After the fixation elements 1, 1a, 1b, 1c have been fitted onto the articular processes, the securing pin 9 is driven into the articular process and both the terminal end of the securing pin 9 and the part of the securing pin 9 situated close to the block-shaped body 4 are located in cortical bone of the articular process, so that the pin 9 in this securing position is capable of taking up considerable couple and the fixation elements 1, 1a, 1b, 1c are firmly affixed to the articular processes.

As is clearly shown in FIG. 1, the longitudinal and transverse wires 2, 2a and 3, 3a, respectively, are detachably connected to the fixation elements 1, 1a, 1b, 1c, the longitudinal wires 2, 2a being connected to the fixation elements so as to fix securing pin 9 in the securing position. In the embodiment shown in FIGS. 1–7, the respective longitudinal and transverse wires 2, 2a, and 3, 3a are received in respective L-shaped slots 10 and 11 extending throughout the height and width, respectively, of the block-shaped body. A first leg of the L-shaped slot 10 terminates in a side surface 12 of the block-shaped body 4 that bounds the first articular process contact surface 7, where this first leg constitutes a receiving slot for the rod or wire 2, 2a. A first leg of the L-shaped slot 11 terminates in the bottom surface 13 of the block-shaped body 4, where it constitutes a receiving slot for the transverse rod or wire 3, 3a. The second leg of the L-shaped slots 10 and 11 extends in the direction of the hook and terminates in a bore extending throughout the height and width, respectively, of the block-shaped body 4. The rod or wire can be fixed in the bore by means of a retaining screw 15, 16, respectively, fitted in the rear wall 14 in line with the second leg and extending into the respective L-shaped slots.

In the embodiment shown in FIGS. 8–11, the longitudinal rods or wires 2, 2a are received in a bore 17 extending throughout the height of the block-shaped body 4'. In this embodiment, too, the rod is fixed in the bore 17 by means of a retaining screw fitted in the rear wall 14' and extending into the bore 17. In this embodiment, the transverse connector wires or rods are mounted on the longitudinal rods. Accordingly, the bores or slots extending throughout the width or the block-shaped body 4' are absent.

It will be clear that the invention is not limited to the exemplary embodiment described, but that various modifications are possible within the framework of the invention. Essential is that for fixing the thoracic and/or cervical vertebral column, use is made of fixation elements capable of gripping the articular processes of the vertebrae.

I claim:

1. A device for fixing at least a part of the human vertebral column, said device comprising two assemblies, each assembly comprising a plurality of fixation elements arranged above each other and at least one rod or wire interconnecting these fixation elements, each fixation element comprising a substantially block-shaped body and a hook extending from a lower edge area of the block-shaped body, a first vertebra contact surface comprising an upright side of the block-shaped body that faces the hook and a second vertebra contact surface comprising a substantially upwardly directed surface of the hook, a securing means, which, when in a securing position, extends at least partly into the space between the first and the second vertebra contact surfaces, said vertebra contact surfaces comprising substantially flat articular process contact surfaces, the first and the second articular process contact surfaces being interconnected through a small radius and forming a V-shaped space therebetween, said two assemblies being arranged substantially parallel, the respective fixation elements of said assemblies being arranged at the same level, the assemblies being connected by means of at least one transverse rod or wire, wherein at least two fixation elements of the respective assemblies, arranged at the same level, comprise transverse connector means interconnecting said two assemblies through cooperation with the transverse rod or wire.

2. A device as claimed in claim 1, wherein an angle of the V-shaped space is in a range of 40°–50°.

3. A device as claimed in claim 1, wherein the securing means comprises a securing pin mounted in the block-shaped body such that said securing pin is movable in a direction of its longitudinal axis and extends substantially perpendicularly to the first articular process contact surface, an end of the securing pin remote from the block-shaped body (4) being located close to a free end of the hook in the securing position.

4. A device as claimed in claim 1, wherein the fixation elements comprise means for detachably connecting the rod or wire interconnecting the fixation elements, said means comprising at least a bore extending throughout a height of the substantially block-shaped body for receiving the rod or wire, wherein a position of the bore with respect to the securing means extending into the V-shaped space is such that a rod or wire arranged in the bore fixes the securing means in its securing position.

5. A device as claimed in claim 4, wherein the bore is part of a substantially L-shaped slot extending through the block-shaped body and throughout a height of the block-shaped body, a first leg of said slot terminating in a side surface of the block-shaped body that bounds the first articular process contact surface and comprising a receiving slot for the rod or wire, a second leg of said slot extending toward the hook and terminating in the bore, the rod or wire being fixable in the bore by means of a retaining screw fitted in a rear wall of the block-shaped body in line with the second leg and extending into the L-shaped slot.

6. A device as claimed in claim 1, wherein the transverse connector means comprise a substantially L-shaped slot extending through the block-shaped body throughout a width of the block-shaped body, a first leg of said slot terminating in a bottom surface of the block-shaped body and comprising a receiving slot for the transverse rod or wire a second leg of said slot extending toward the hook, the transverse rod being fixable in the second leg of the L-shaped slot by means of a retaining screw fitted in a rear wall of the block-shaped body in line with the second leg and extending into the L-shaped slot.

7. A device as claimed in claim 6, wherein the securing means comprises a securing pin mounted in the block-shaped body such that said securing pin is movable in a direction of its longitudinal axis and extends substantially perpendicularly to the first articular process contact surface, an end of the securing pin remote from the block-shaped body being located close to a free end of the hook in the securing position.

8. A device as claimed in claim 6, wherein the fixation elements comprise means for detachably connecting the rod or wire interconnecting the fixation elements, said means comprising at least a bore extending throughout a height of the substantially block-shaped body for receiving the rod or wire, wherein a position of the bore with respect to the securing means extending into the V-shaped space is such that a rod or wire arranged in the bore fixes the securing means in its securing position.

9. A device as claimed in claim 8, wherein the bore is part of a substantially L-shaped slot extending through the block-shaped body and throughout a height of the block-shaped body, a first leg of said slot terminating in a side surface of the block-shaped body that bounds the first articular process contact surface and comprising a receiving slot for the rod or wire, a second leg of said slot extending toward the hook and terminating in the bore, the rod or wire being fixable in the bore by means of a retaining screw fitted in a rear wall of the block-shaped body in line with the second leg and extending into the L-shaped slot.

* * * * *